United States Patent [19]

Rollins, III et al.

[11] 4,328,797
[45] May 11, 1982

[54] NASO-GASTRIC OXYGEN MASK

[76] Inventors: Offord L. Rollins, III; Anthony F. Williams, both of 3772 Lockland Dr., #20, Los Angeles, Calif. 90008

[21] Appl. No.: 171,644

[22] Filed: Jul. 23, 1980

[51] Int. Cl.³ .............................................. A61M 16/00
[52] U.S. Cl. ........................... 128/202.27; 128/202.15; 128/205.25; 128/206.21; 128/206.24; 128/912; 128/207.13
[58] Field of Search ....................... 128/205.25, 203.29, 128/206.21, 206.24, 206.28, 206.29, 207.12, 207.13, 207.14, 207.18, 202.15, 912, 202.27

[56] References Cited

U.S. PATENT DOCUMENTS

| | | | |
|---|---|---|---|
| 2,023,267 | 12/1935 | DeSaint Rapt et al. | 128/202.15 |
| 2,675,803 | 4/1954 | Kaslow | 128/205.25 |
| 2,831,487 | 4/1958 | Tafilaw | 128/207.18 |
| 2,859,748 | 11/1958 | Hudson | 128/206.28 |
| 3,067,425 | 12/1962 | Colley | 128/202.15 |
| 3,357,426 | 12/1967 | Cohen | 128/202.27 |
| 3,388,705 | 6/1968 | Grosshandler | 128/912 |
| 3,730,179 | 5/1973 | Williams | 128/207.18 |
| 4,201,205 | 5/1980 | Bartholomew | 128/205.25 |

FOREIGN PATENT DOCUMENTS 503739  6/1964  Canada ........................... 128/207.18

Primary Examiner—Henry J. Recla

[57] ABSTRACT

A mask for delivery of gas, such as oxygen, to a patient and useable in a naso-gastric intubation procedure without disruption of the seal between the mask and the face of the patient. The body of the mask includes a fenestration or opening through which the naso-gastric tube may be inserted. The fenestration is preferably shaped to support the tube in manner which is comfortable for the patient and which eliminates or minimizes the amount of gas lost to the atmosphere outside the mask. In at least some embodiments, the fenestration is closed when a tube is not inserted therethrough so that the mask may be used normally without loss of the gas through the fenestration.

24 Claims, 15 Drawing Figures

NASO-GASTRIC OXYGEN MASK

TECHNICAL FIELD

This invention relates to the field of masks, and more specifically those masks which are used to administer a gas, such as oxygen, to a patient, particularly when a naso-gastric intubation procedure is to be accomplish simultaneously.

BACKGROUND OF THE INVENTION

The administration of gas, and particularly oxygen, to a patient is often lax and/or unsatisfactory. The administration, regulation, and efficiency are very poor since a relatively unknown volume of oxygen is delivered to the patient. For the most part, a simple oxygen mask or a nasal cannula of one type or another is normally used for the routine administration of oxygen.

A wide variety of oxygen masks have been available, varying in construction, style, and material, depending upon the specific purpose for which each is desired to be employed. Until recently, most masks were made of rubber. As a result of the need to provide a mask which is inexpensive, requires little storage space, need not be sterilized, and can be disposed of after each use to minimize contamination, most oxygen masks presently in use are made of plastic.

The basic mask which is available today uses neither a valve nor a reservoir bag. Exhaled air from the lungs of the patient is usually vented through holes in the body of the mask. In view of its convenience and relative comfort, the basic mask is widely used whenever moderate oxygen concentrations are desired for short periods of time. This might occur, for example, during the postoperative recovery state of a patient. Such a mask might also be used, for example, during either temporary or interim therapy when a patient is being weaned from continuous oxygen administration.

Most masks available today are relatively crude, causing a prediction of the exact volume of oxygen delivered to the patient to be impossible. However, it is known that the delivered concentrations vary from 35% to 55%, at gas flow rates of 6 to 10 liters per minute.

The nasal cannula is an appliance which normally includes two tips which extend from an oxygen supply tube and are inserted into the nostrils of a patient. The cannula can be held in place by head straps or by bows that hook over the ears, in the manner of eye glasses.

Unfortunately, the cannula suffers from the disadvantage of being instable, i.e., it is easily dislodged from a restless or unobservant patient. While a doctor or nurse making medical rounds might note that an oxygen flow meter is open, he or she might not notice that the cannula is so twisted out of place that the patient could not get any significant amount of oxygen.

The cannula also suffers from the disadvantage that it is often necessary to pay attention to a patient's comfort when instituting oxygen treatment. An excessive flow rate of oxygen, the definition of which varies according to the patient, can produce a considerable amount of pain in the frontal sinuses of the patient. Also, such nasal pathology as a deviated septum, mucosal edema, mucus drainage, and polyps may interfere with a patient's oxygen intake.

In those cases in which a naso-gastric tube might be used together with the nasal cannula, the utility of the latter is further degraded. In addition to dislodgement problems, the combined affect of the two tubes placed in one nostril creates a physical irritant to the delicate mucosal tissues of the nasal passage and sinuses. Such irritation often takes the form of ulcerative lesions. Since a decreased volume of oxygen is often experienced during the use of the two tubes, the normal procedure is to increase the rate of oxygen flow. However, that often results in the desiccation of tissues, further traumatizing them, causing severe frontal sinus pain and various pathalogic results.

Consequently, it is believed that the basic oxygen mask having a body which is pressed against the face of the patient is far superior to the nasal cannula for the application of oxygen. Nevertheless, such masks suffer from the disadvantage that, in many postoperative and related cases, a naso-gastric intubation procedure is necessary. In such a case, plastic tubing is usually inserted into the patient's nasal passageway and guided down the esophagus into the upper gastric area. This tubing is an obstruction, as far as the administration of oxygen is concerned, and complicates the application of the mask or the cannula.

If, today, a naso-gastric tube and an oxygen mask are to be used simultaneously, the tube is put in place first and the mask is then applied. The seal of the mask against the face of the patient is incomplete due the protrusion of the tube at the point that the tube intersects the body of the mask. In other words, it is impossible to conform the mask to the facial configuration of the patient and, in many cases, the mask is generally askew. Such incorrect seating of the mask allows oxygen to freely pass to the atmosphere, resulting in treatment of the patient with a decreased and uncontrolled volume.

Additionally, the stability of the mask as well as the patient's comfort are complicated by the tube. The mask is much less secure and more easily dislodged by an unobservant, restless, or mobile patient. Also, the tube is usually placed across and secured to the facial skin in an attempt to prevent relative movement among the patient, tube, and mask. The taping of the tube to the skin often produces discomfort and runs the risk of producing a pressure necrosis of the skin.

An example of a prior art mask which may be used together with a naso-gastric tube in the manner described above has been illustrated in U.S. Pat. No. 3,357,426 to Cohen. The drawings of that patent clearly depict the manner in which the naso-gastric tube is located on the face of the patient in such a manner as to prevent a complete seal about the edge of the mask body, rendering the mask less stable on the face of the patient.

On the other hand, U.S. Pat. No. 3,809,079 to Buttaravoli discloses a combined resuscitation mask and airway for ventilation of a patient's lungs in a positive and reliable manner. However, that disclosure includes a rigid body which may extend down the throat of the patient; it does not relate to a structure which would facilitate a naso-gastric intubation.

Consequently, a need currently exists for a oxygen-administration device which may be simultaneously employed with a naso-gastric tube in such a manner that the volume of oxygen can be controlled at least to the same extent as may be attained with a fully seated oxygen mask.

SUMMARY OF THE INVENTION

The present invention relates to an oxygen mask which may be employed in the well-known manner. Such a mask is produced, for example, by Ideal Medical Products of Lansing MI. A mask which can be utilized with the present invention may be of any desired size, configuration, etc. Preferably, the mask is relatively pliable, such as might be the case with a soft, clear vinyl, and easily adaptable to the facial contours of the patient in order to provide sealing throughout the periphery of the mask body where it contacts the skin of the patient.

More specifically, the present invention relates to such a mask which is adapted to particularly provide for the passage of a tube therethrough, such as that which might be employed in a naso-gastric intubation procedure.

The present invention, which may be employed in a wide variety of embodiments, basically comprises a fenestration in the wall of the mask body. When a tube is not in place in the fenestration, the latter will be substantially closed so as to minimize or completely prohibit any escape therethrough of oxygen from the interior of the mask body.

In the presently preferred embodiment, the fenestration may be provided adjacent to and extending through the sealing portion of the mask. The fenestration may be located at any desired position about the periphery of the mask so that a tube may be so arranged as to be substantially and comfortably aligned with the nostril of the patient.

The fenestration may be of any desired size and configuration. In many cases, however, it will be preferred that the fenestration be of such a configuration that it will firmly hold the naso-gastric tube in place without allowing relative movement between the tube and the mask. In some embodiments, it is currently preferred that the fenestration be provided with some type of lining material or other structure which will provide a form of seal, either about the tube, or across the fenestration itself so that the opening is sealed when a tube is not in place. The invention allows this type of mask to be used with or without a naso-gastric tube, with little or no difference, in the placement of the mask and the availability of the oxygen to the patient.

Upon review of the following Detailed Description, taken together with the accompanying drawings, those skilled in the art will realize that the present invention may be employed in a wide variety of embodiments, many of which may not even resemble those described and depicted here. Nevertheless, it should be borne in mind that that the description and accompanying drawings are merely illustrative of the principles of the present invention and only set forth the best mode presently contemplated for accomplishing the invention. They are not intended to delimit or restrict the scope of the invention which is defined and limited only by the appended claims.

DETAILED DESCRIPTION

Figure 1:
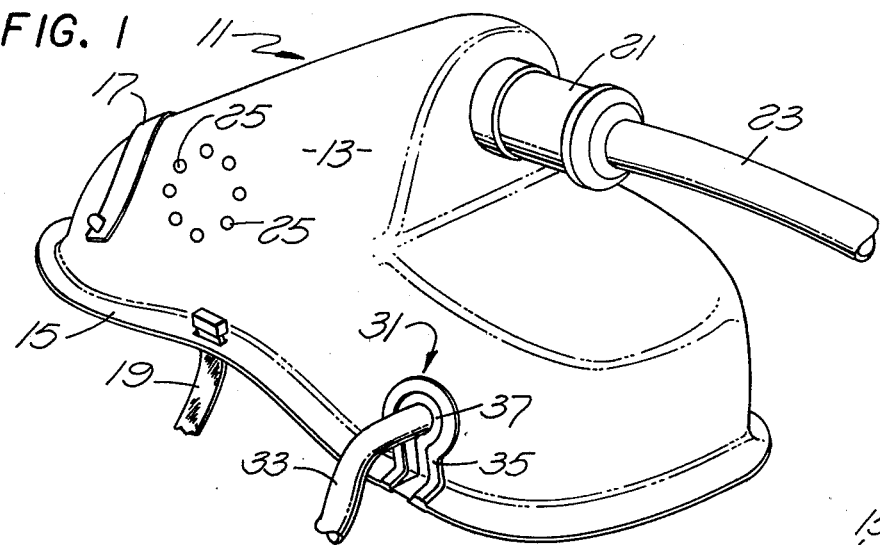
FIG. 1 comprises an isometric illustration of a mask formed in accordance with the present invention, depicting the use of a fenestration in the wall of the mask.

Referring now to FIG. 1 in greater detail, a mask 11 is shown including a body 13 which surrounds an internal cavity. The body 13 may be placed over the nose and mouth of a patient so that the patient may inhale and exhale into the mask cavity. The periphery of the body 13, at the open edge of the cavity, is preferably surrounded by a sealing surface 15 which may be placed against the patient's face to prevent the passage of gas or oxygen in or out of the mask cavity except through preselected passages. In the current state of the art, the mask body 13 and sealing lip 15 are preferably constructed of transparent, thin, pliable plastic which is relatively inexpensive. Consequently, the mask readily conforms to any patient's face. It can be easily used and then disposed of without risking cross-contamination of patients, requiring cleaning between uses, etc.

If desired, the upper portion of the mask may be provided with a pliable nose piece 17 which may be bent to generally conform to the nose of the patient. The nose piece assists in holding the mask in place and keeping it sealed against the patient's face. Similarly, the mask may be provided with a band, strap or earpiece in order to hold the mask to his face.

In the particular type of mask illustrated, a relatively rigid inlet connection device 21 may be fixedly attached to the mask body 13 for receipt and support an oxygen or other gas hose 23. Thus, oxygen can be fed through the hose 23 into the mask 13 through the connector 21 for increasing and controlling the oxygen intake of the patient. In order to allow the exhaled breath of the patient to be exhausted from the mask, one or more aperatures 25 may be provided in either or both sides of the mask.

As described thus far, such masks are currently readily available and constitute prior art, of which this invention is an improvement.

Figure 2:
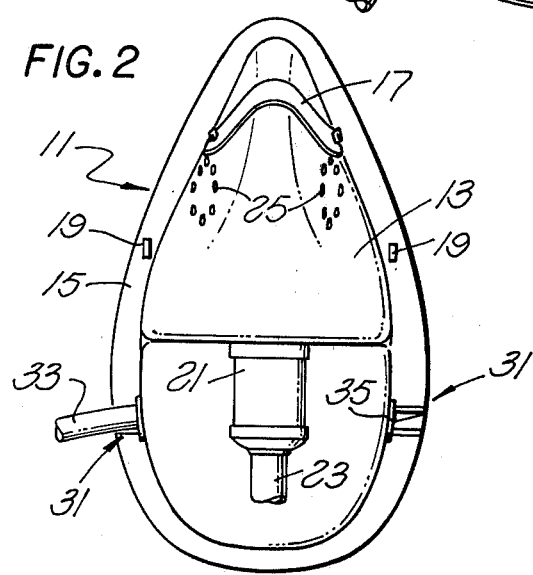
FIG. 2 comprises a top plan view of the mask depicted in FIG. 1 depicting a fenestration on each side of the mask.

As seen in FIG. 1, the mask may be provided with a cleft or fenestration 31, through which a naso-gastric tube 33 may pass and within which it may be secured. Of course, those skilled in the art will realize that, as shown in FIG. 2, two clefts or fenestrations may be provided for the passage of a like number of naso-gastric tubes. In any event, it is preferred that the cleft or fenestration 31 be so positioned as to allow comfortable and convenient aligned of a tube 33 with the nostril of a patient so that the use of the mask and the naso-gastric tube will not conflict with one another in servicing the patient.

In the embodiment illustrated in FIG. 1, the fenestration 31 is shown shaped in a form similar to a "key hole" 35 having a foam rubber or other flexible lining 37 which may be split down the middle for insertion and receipt of the tube 33. The lining and the central slit or opening therein preferably extend down to and through the sealing portion 15 of mask 11. Consequently, proper selection of the liner 37 will allow the slit to remain substantially closed throughout the entire length of the fenestration 31 when a tube, such as that illustrated at 33, is not in place. On the other hand, when the tube 33 is installed, the lining 37 will closely surround the tube and be substantially closed throughout its length for the remainder thereof.

As a result, such a fenestration will produce a significant advancement in the technology of therapeutic application of oxygen simultaneously with the use of a naso-gastric tube. The volume of oxygen applied will be relatively precise in accordance with the orders of the doctor to the medical personnel.

In use, the naso-gastric tube would be applied to a patient in the well-known manner. The mask may then be placed in position against the face of the patient. The cleft or fenestration 31 may be manually split and pushed over the tube 33 until the tube is located in the upper portion of the slit or opening. Thus, the tube may be substantially sealed and firmly seated in the upper portion of the key hole-shaped opening and the mask will remain sealed against the face of the patient.

Figure 3:
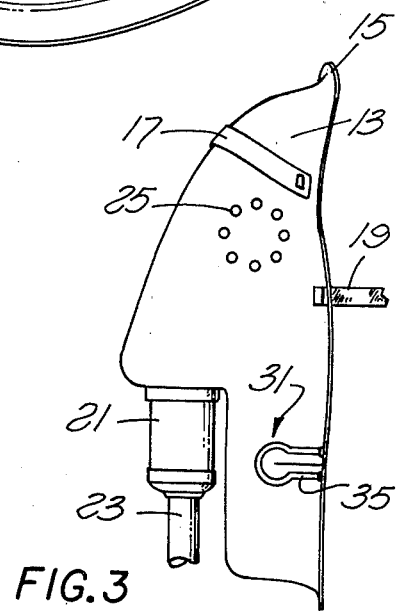
FIG. 3 comprises a side elevation view of the mask depicted in FIGS. 1 and 2.
Figure 4:
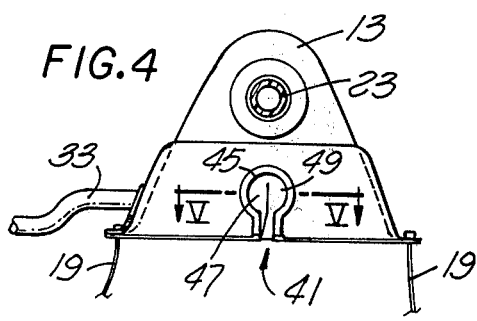
FIG. 4 comprises an elevation view of the bottom end of a second mask embodiment formed in accordance with the present invention, illustrating a single fenestration in the base end of the mask.
Figure 5:
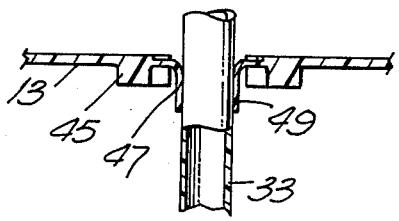
FIG. 5 comprises a sectional plan view of the mask shown in FIG. 4, as seen along a line V—V therein.

Referring now to FIGS. 4 and 5, an alternate embodiment of the device shown in FIGS. 1-3 has been illustrated. In that embodiment, the fenestration 41 may comprise a slit formed in the bottom portion of the mask and extending upwardly from the sealing 15 to a location intermediate the seal and the connector 21.

A rib 45 may be formed integral with or suitably attached to the body 13 about the vicinity of the slit, thus preventing stress, imposed when the tube is installed, is in place, and/or is removed, from damaging the mask. Thus, with this embodiment, the edges of the slit, i.e., the adjacent portions of the mask body 13, will form a pair of flaps 47 and 49 which are normally closely adjacent one another to seal off the fenestration.

When the mask is placed over a tube 33, the fenestration may again be manually split and pushed over the tube. When the tube reaches the upper portion of the split, it will thus be seated and substantially sealed therein. The fenestration may then be closed so that the flaps 47 and 49 are as close together as possible. As a result, the naso-gastric tube can be properly positioned and will not move about if the patient should be become restless or mobile. At the same time, the mask will continue to be sealed against the patient's face at all times to provide the optimum sealing effect. Any oxygen loss through the fenestration slit between flaps 47 and 49 will be minimal since any separation therein will be relatively small.

Referring now to FIGS. 6-15, it can be seen that a wide variety of shapes, sizes, etc., of clefts or fenestrations may be employed, realizing that they may be used singly or in pairs and at any convenient location in the mask so as to properly hold the naso-gastric tube in a convenient and comfortable location for the patient.

Figure 6:
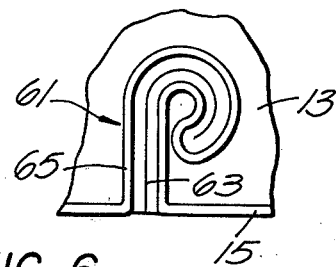
FIGS. 6–15 depict various shapes and configurations of fenestrations which may be employed in a facial mask in accordance with the present invention.

In FIG. 6, for example, it can be seen that the mask body 13 may be provided with a fenestration 61 having a slit 63 therein and a reinforcing wall or rib 65 spaced from the rib a convenient distance for allowing the insertion and position maintenance of a tube (not shown). In this illustrated embodiment, the fenestration 61 may be formed in a shape resembling a crook of a sheppard's staff. Consequently, when the mask is installed over the tube, the latter may be moved into the inner end of the slit to provide substantial sealing of the tube and also to firmly ensure that it is properly seated and held in place.

If desired, of course, the internal end portion of the fenestration 61 may be enlarged so as to provide an opening of substantially the same size as that for the cleft 31 shown in FIG. 1. Also, it will be realized by those skilled in the art that the slit 63 may be formed in the wall of the body 13 similarly as shown in FIG. 5, or it may be provided between opposed edges of a foam rubber liner, similar to that structure shown in FIG. 1. In either case, the slit will be substantially closed with the tube in place, again minimizing inadvertant oxygen loss.

Figure 7:
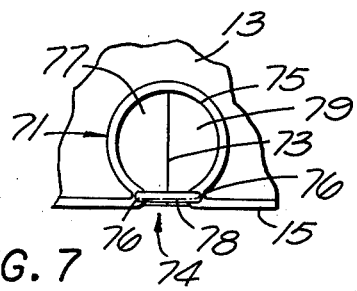

Referring now to FIG. 7, a fenestration 71 is illustrated having a slit 73 for receipt of a naso-gastric tube. The vicinity of the slit 73 may be substantially surrounded and strengthened by a rib or wall 75 of substantially circular configuration. Thus, with the tube in place, the fenestration may be manually split, such as by pulling one side away from the mask cavity and pushing the other side into the cavity, may then be gently pushed down over the tube. When the tube is substantially surrounded by the rib 75, the opposite sections of the cleft 71 may be realigned, thus holding the tube in place with a substantial seal about the periphery thereof through the actions of flaps 77 and 79. Once again, flaps 77 and 79 may be part of the wall of mask body 13 or they may be separate, attached elements.

If desired, this fenestration may be held in the closed position during use, such as by means of a suitable clasp 74 which may include one or more protrusions 76 and a cross-piece 78. Alternatively, the protrusions may be used to located and hold a small rubber band or similar element to hold the fenestration closed. Although shown only in this embodiment, those skilled in the art will readily realize that such a positive closure may be used with any fenestration.

Figure 8:
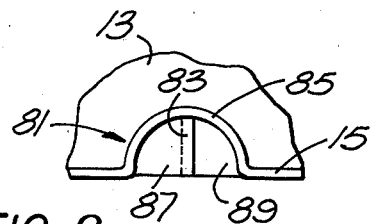

Another embodiment of a fenestration is illustrated in FIG. 8 at 81. In this instance, a strengthening rib or wall 85 may be provided on opposite sides of a pair of flaps 87 and 89. The flaps may either be integral with the wall of the body 13 or specifically attached thereto. In any event, each flap may be provided with a square side edge so that the flaps normally overlap. Alternatively, the slit 83 may be formed by cutting the portion of the wall 13 below the rib 85 on an acute angle or bias relative to the surface of the wall. Thus, when the flaps 87 and 89 are aligned, the opposed surfaces of the slit, which are at an identical acute angle relative to the wall 13, will abut one another and serve to seal the fenestration.

When it is desired to use such a mask with a naso-gastric tube, it is only required that the medical personnel gently push the mask down over the tube. Thus, the tube will be substantially sealed in place and the mask will still fit closely against the face of the patient without undue loss of oxygen.

Figure 9:
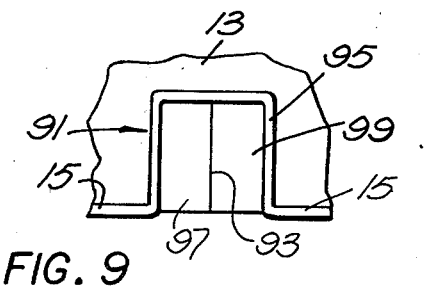

As shown in FIG. 9, a fenestration 91 may be provided of substantially rectangle configuration having a slit 93 bounded by a rib or wall 95. In this instance, the slit is illustrated as having a squared edge between opposed flaps 97 and 99, although those skilled in the art will realize that a biased slit could also be provided in the manner of that illustrated in FIG. 8. Alternatively, the flaps 97 and 99 could be slightly enlarged so that the adjacent edges thereof overlap to provide a more positive sealing when a tube is not in place.

Once again, when a fenestration such as that at 91 is to be employed, it is simply necessary to install the tube and then push the mask down over the tube so that it is sealed by the flaps 97 and 99 for minimal oxygen loss.

Figure 10:
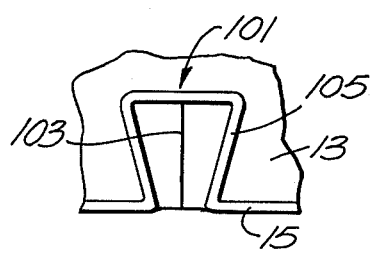

Referring now to FIG. 10, a fenestration 101 may be provided with a slit 103 bounded by a strengthening rib or wall 105 resembling an inverted, truncated triangular configuration. With this structure, when the mask is to be applied over the tube, the opposite ends of the slit adjacent the sealing edge of the mask may again be manually split and the tube gently pushed over the mask. The ends may then be manually realigned to hold the tube in place and substantially seal it to achieve the desired result.

Figure 11:
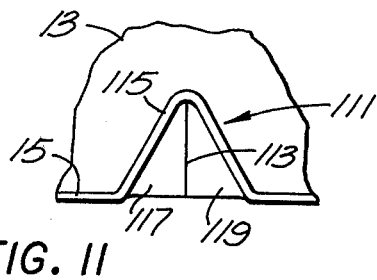

The fenestration 111 illustrated in FIG. 11 is shown as comprising a slit 113 bounded by a rib 115 having two legs which meet at an acute angle, i.e., resembling two legs of an isosceles triangle. Consequently, when a mask using this type of cleft is pushed down over a tube, opposed flaps 117 and 119 will part and allow the tube to be substantially sealed in position while the mask is still sealed to the face of the patient throughout the remainder of its periphery.

Figure 12:
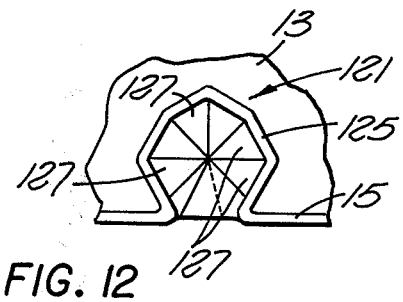

A still further embodiment of a fenestration is illustrated at 121 in FIG. 12. In this illustration, a multisided polygonal rib 125 may provide the external boundary for a plurality of flaps 127 which are separated by slits in the wall material of the body 13. Preferably, the number of flaps is equal to or greater than the number of sides of the polygon. Thus, this mask may be employed by manually misaligning the opposite edges of the fenestration adjacent the sealing lip 15 and pushing the mask down over the tube. The flaps 127 will part along the slits at their respective edges, allowing the tube to be held in place and substantially sealed when the opposite edges of the fenestration are again realigned.

Figure 13:
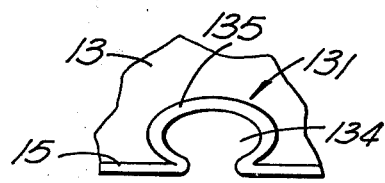
Figure 14:
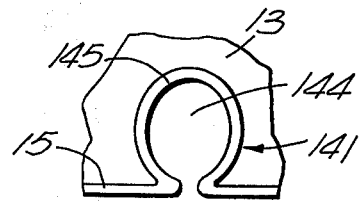

As shown in FIGS. 13 and 14, in some instances it may be desired to provide an open fenestration such as the ovoid configurations illustrated at 131 or that illustrated at 141. The opening 134 or 144 may be provided with a generally oval-shaped ridge 135 or 145, respectively. Such masks may also be applied by temporarily misaligning the opposite edges of the fenestration adjacent the sealing lip and then realigning them after the mask is pushed over the tube. It will often be preferable to use structures such as those shown in FIGS. 13 and 14 when the shape of the open fenestration is substantially identical to that of the tube to be used, thus allowing the tube to be sealed against the rib or wall of the fenestration and also be held in place by the alignment of the lower portions of the fenestration against the sealing lip 15.

Figure 15:
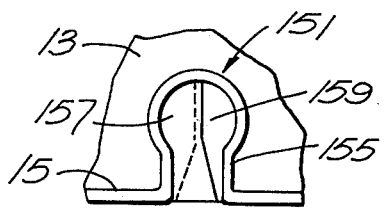

Of course, those skilled in the art will realize that a cleft or fenestration such as those found in this disclosure may be provided with any kind of sealing means or structure which substantially seals and holds the mask in a fixed relationship with the naso-gastric tube. As shown in FIG. 15, for example, a key hole-type fenestration 151 may be provided with a rib 155 which abounds an opposed pair of overlapping flaps 157 and 159. Thus, as illustrated, it is not necessary that the flaps meet one another along a single, clean line. It is only necessary that the fenestration be substantially closed when a naso-gastric tube is not in place in the patient and also substantially closed and sealed about the tube when the patient is undergoing naso-gastric intubation and oxygen therapy simultaneously.

As a result of a review of the various embodiments of this invention, it should now be apparent to those skilled in the art that the oxygen mask fenestration or cleft which may be utilized with any particular tube or similar devices may be of any desired size or shape, depending only upon the particular apparatus which is extend therethrough. Similarly, any suitable sealing device may be employed in the fenestration, including opposed flaps, a liner, or a reasonably close tolerance fit between the tube and the rib which strengthens the opening. Also, even simpler embodiments may be employed.

For example, the mask body 13 might simply be provided with an aperture through which a tube may extend in reasonably close relationship. For tube installation purposes, a slit may extend from the aperture through the sealing lip 15. As packaged or used without a tube, the aperture and slit may be closed or covered by a small piece of tape which can be manually removed when necessary. When a tube is in place within the aperture, the slit may be retaped to close it, strengthen the mask (particularly if no rib such as that at 45 is used), and hold the tube in place.

Having now reviewed this Detailed Description and the drawings of the presently preferred embodiment, those skilled in the art will realize that these merely define a presently preferred embodiment of the invention instead of delimitating it. Rather, it must be kept in mind that the scope of the invention, as set forth below, is broad enough to encompass a substantial number and wide variety of embodiments, many of which may not even resemble that depicted and described here. Nevertheless, such additional embodiments will employ the spirit and scope of the invention which is established only by the following claims.

We claim:
1. A face mask for the administration of a gas such as oxygen comprising
    a mask body of such size and shape adapted to cover at least the nose of a patient and having a peripheral edge;
    means for holding the mask against the face of a patient;
    means for directing a flow of a gas to the interior of the mask;
    means about the peripheral edge of the body for substantially sealing at least a portion of the body of the mask against the skin of the patient; and
    means for admitting a naso-gastric tube into the interior of the mask body for insertion into the nostril of the patient comprising
        a fenestration in the body extending through the peripheral edge and sealing means and located in a convenient position for allowing the passage of the tube through the fenestration and into the nostril of the patient, and
        means for substantially closing the fenestration to prevent the loss therethrough of gas directed into the mask body by the directing means.
2. The mask of claim 1 wherein
the fenestration includes
    means on the mask body including
        a slit through which a naso-gastric tube may be passed and seated near one end thereof,
        means on either side of and defining the slit for substantially sealing a naso-gastric tube therebetween.
3. The mask of claim 2 wherein
the sealing means comprises a sealing liner extending throughout the fenestration and including opposed sealing portions therein defining the slit.

4. The mask of claim 2 wherein
the sealing means comprises means integral with the mask body and defining the slit therebetween.

5. The mask of claim 3 or 4 including
means extending about at least a portion of the fenestration for strengthening the mask body to prevent damage thereto as a naso-gastric tube is installed and seated in the fenestration.

6. The mask of claim 5 wherein
the fenestration includes means for holding the fenestration closed.

7. The mask of claim 1 or 2 including
means extending about at least a portion of the fenestration for preventing damage to the mask body as a tube is installed within the fenestration.

8. In an oxygen mask including a mask body adapted to cover at least the nose of a wearer and having a peripheral edge and a sealing means extending about the peripheral edge of the body for substantially sealing the mask to the face of a wearer,
a fenestration formed in the body and extending through the peripheral edge and sealing means, and
means in the fenestration for accepting and seating a naso-gastric tube therein.

9. The mask of claim 8 including
means for substantially sealing the tube in the fenestration when the former is seated therein to minimize the loss of oxygen through the fenestration.

10. The mask of claim 9 wherein
the sealing means comprises a liner positioned within the fenestration and having a central slit extending substantially therethrough and being openable in the vicinity of the sealing means.

11. The mask of claim 9 wherein
the sealing means comprises at least two opposed flaps located on opposite sides of the fenestration for holding and sealing a tube therebetween.

12. The mask of claim 9 wherein
the sealing means comprise a plurality of flaps so situated within the fenestration as to hold and seal a tube therebetween.

13. The mask of claim 8, 9, 10, or 12 including
strengthening rib means located about the fenestration to prohibit damage to the mask as a naso-gastric tube is installed and seated in the fenestration.

14. The mask of claim 13 including
means for holding the fenestration closed at the end thereof extending through the sealing means.

15. The mask of claim 8 wherein
the fenestration is shaped in a form generally resembling a keyhole with the enlarged portion thereof distal from the sealing means for seating the tube when the fenestration is closed.

16. The mask of claim 8 wherein
the fenestration is shaped in a form generally resembling
the crook of a shepards staff wherein an inner end thereof is provided for seating the tube therein.

17. The mask of claim 8 wherein
the fenestration is shaped in a form generally resembling
a circle having an open portion at the sealing means for movement of the mask onto the tube.

18. The mask of claim 8 wherein
the fenestration is shaped in a form generally resembling
a semicircle having an open portion at the sealing means for movement of the mask onto the tube.

19. The mask of claim 8 wherein
the fenestration is shaped in a form generally resembling
a rectangle having an open portion at the sealing means for movement of the mask onto the tube.

20. The mask of claim 8 wherein
the fenestration is shaped in a form generally resembling
a truncated triangle having an open portion at the apex thereof at the sealing means for movement of the mask onto the tube.

21. The mask of claim 8 wherein
the fenestration is shaped in a form generally resembling
an isosceles triangle having an open portion at the sealing means for movement of the mask onto the tube.

22. The mask of claim 8 wherein
the fenestration is shaped in a form generally resembling
a polygon having a number of accepting and seating means therein at least equal to the number of sides of the polygon and having an open portion at the sealing means for movement of the mask onto the tube.

23. The mask of claim 8 wherein
the fenestration is shaped in a form generally resembling
an ovoid having an open portion at the sealing means for movement of the mask onto the tube.

24. The mask of claim 8 wherein
the fenestration is shaped in a form generally resembling
a keyhole including overlapping sealing flap therein with the enlarged portion thereof distal from the sealing means for seating of the tube between the sealing flaps when the fenestration is closed.

* * * * *